United States Patent [19]
Wright et al.

[11] Patent Number: 4,850,868
[45] Date of Patent: Jul. 25, 1989

[54] SPRAY SHIELD

[75] Inventors: Gerard Wright, Irvine, Calif.; George E. Warrin, North Merrick; Richard H. Paschke, Medford, both of N.Y.

[73] Assignee: Dentsply Research & Development Corp., Milford, Del.

[21] Appl. No.: 72,471

[22] Filed: Jul. 13, 1987

[51] Int. Cl.⁴ ............................................. A61C 1/16
[52] U.S. Cl. ..................................... 433/116; 433/80; 128/62 A
[58] Field of Search ...................... 433/80, 82, 83, 86, 433/87–91, 116, 119, 136, 139, 29; 128/66, 62 A; 239/103, 104; 406/157, 196, 194; 285/239, 240

[56] References Cited

U.S. PATENT DOCUMENTS

| | | |
|---|---|---|
| 1,988,979 | 1/1935 | Campbell . |
| 2,978,186 | 4/1961 | Mayerchak ........................ 239/103 |
| 3,215,350 | 11/1965 | Hetrick ........................... 239/104 X |
| 3,391,696 | 7/1968 | Woodward . |
| 3,426,750 | 2/1969 | Clements .............................. 128/66 |
| 3,747,216 | 7/1973 | Bassi et al. .......................... 433/81 |
| 4,412,402 | 11/1988 | Gallant . |
| 4,611,992 | 9/1986 | Lokken ............................ 433/80 X |

FOREIGN PATENT DOCUMENTS

| | | |
|---|---|---|
| 0127380 | 12/1984 | European Pat. Off. . |
| 0143617 | 6/1985 | European Pat. Off. . |
| 3447744 | 7/1986 | Fed. Rep. of Germany . |

*Primary Examiner*—Larry Jones
*Attorney, Agent, or Firm*—David E. Wheeler; Edward J. Hanson, Jr.

[57] ABSTRACT

The apparatus comprises a tubular member that is adapted to be attached to the working end of a dental handpiece and is used to contain and direct material dispensed from the handpiece in order to reduce the amount of airborne particles emitted into the atmosphere by the handpiece and to accurately direct the dispensed material to the desired area. The apparatus is adapted to provide a reference point for the practitioner in establishing the optimum working distance of the handpiece from a particular working area in the mouth when the handpiece is used. An improved dental handpiece using the apparatus of the invention and a method of using the apparatus are also provided.

6 Claims, 1 Drawing Sheet

SPRAY SHIELD

BACKGROUND OF THE INVENTION

The present invention relates to a spray shield for dental handpieces that can be used to minimize the amount of material that escapes into the air when using a dental handpiece, and to direct the spray of the material on a working surface and can be used, for example, with a handpiece which is used to abrasively clean teeth.

Stains on teeth may originate from various sources or causes including smoking, tabacco chewing, excessive drinking of tea or from vegetable origin. Calculus is of several different types, especially serumal and salivary, and calculus deposits ordinarily form in pockets between the teeth and the surrounding soft tissues, the serumal calculus originating from the saliva. These constituents precipitate and bond themselves to the exposed tooth surfaces.

It is known in the art to clean teeth using air-abrasive equipment which is particularly useful for removing stains from crevices in the teeth.

By air-abrasive equipment, it is meant that an apparatus, particularly a dental handpiece, is provided in which a gas propels a mildly abrasive powder and preferably a liquid against a tooth surface, for example, to clean teeth using a mildly abrasive mixture of said powder and liquid. The equipment is called air-abrasive since the gas used for propelling the powder will preferably be air.

In the use of air-abrasive equipment for dental purposes, the delivery and dispersal of abrasive particles in air suspension in the mouth is objectionable and in some prior equipment employed for tooth cutting, vacuum means has been employed to capture the abrasive particles. This, however, is bulky and cumbersome. In some prior systems it has also been contemplated to wash the teeth with water following the abrasive treatment, but such subsequent washing does not overcome the objectionable initial distribution of the abrasive particles on the soft tissues and other parts of the mouth. To alleviate these difficulties and to provide air-abrasive prophylaxis equipment adapted to the convenient and effective removal of stain and or calculus in a manner which is simple and which produces minimum discomfort to the patient, a handpiece was provided having a nozzle with an air-abrasive discharge passage, and a water discharge passage surrounding the air-abrasive passage, together with control means by which warmed water was delivered for discharge through the water passage, and the air-abrasive and water streams were coordinated to capture the abrasive particles after they were dispensed.

In the handpiece provided in the prior art, the water discharge passage is directed to impinge upon the surface of the tooth being cleaned in an area immediately adjacent to or overlapping the area of impingement of the air-abrasive stream. Preferably a water stream is provided to form a curtain surrounding the air-abrasive stream. In its most effective embodiment, the motion of the powder and liquid as it is being dispensed from the handpiece causes a mixing of the powder and water to form a slurry. It is an air propelled slurry of abrasive powder and water which provides the most effective cleaning of teeth.

Although forming a slurry greatly minimizes the amount of material that escapes into the atmosphere, under the pressure used in the handpiece, it is inevitable that at least some of the fine spray or mist of material will escape into the atmosphere.

Also, as now presently used, the above described handpieces are held in the hand a recommended distance from the working area which is estimated by the practitioner. If the handpiece is held too far from the working area, it is difficult for the practitioner to avoid hitting restorative areas or sensitive gingival tissue in the mouth which can be damaged.

Also, it is sometimes difficult for the practitioner to see where he is cleaning in the posterior areas of the mouth, and there is a need in the art for a device by which the practitioner can maintain a desirable working distance by other means when using a tool for air-abrasive cleaning of teeth.

It is the object of the present invention to overcome the above described problems in the prior art.

SUMMARY OF THE INVENTION

The apparatus of the invention is adapted for use with a dental handpiece. The apparatus comprises a tubular member having a first end adapted to be attached to the working end of the handpiece, and a second end adapted to extend a fixed distance beyond the working end of the handpiece. The tubular member is adapted to direct the flow and temporarily contain material dispensed from said handpiece. The tubular member also is a means for maintaining a substantially optimum working distance between the handpiece and the working area on which the dental handpiece is used. The tubular member is elastomeric to a degree sufficient to stretch and fit over the working end of the handpiece and to be held tightly on the end of the handpiece. The portion of the tubular member that extends beyond the end of the handpiece has a length adapted to provide a substantially optimum and constant working distance for the operator of the handpiece from the working area when the second end of the tubular member is held in close proximity to the working area.

An improved dental handpiece, wherein the improvement is the spray shield of the invention is also provided.

A method of using the apparatus of the invention with a dental handpiece is also provided.

The apparatus and method of the present invention minimizes the amount of particles that escape into the atmosphere by containing the spray of materials within the apparatus until the initial power of their initial dispensing from the handpiece is diminished. The apparatus of the invention also makes it possible for the practitioner to more precisely control the area of impact of the spray since the spray is directed through the apparatus of the invention, making it easier to avoid hitting restorative areas and gingival tissue with the spray. The apparatus also increases the efficiency of the procedure since the second end of the tubular member in close proximity to the working area provides a reference point for maintaining what may be considered the optimum working distance of the handpiece from a particular working surface. Also, the practitioner may use the apparatus of the invention for better cleaning posterior regions of the mouth by adapting the length of the second portion of the spray shield to what may be considered the optimum length, and holding the second end directly agaisnt or on an angle against posterior teeth to provide a cleaning thereof.

DETAILED DESCRIPTION OF THE INVENTION

Figure 1:
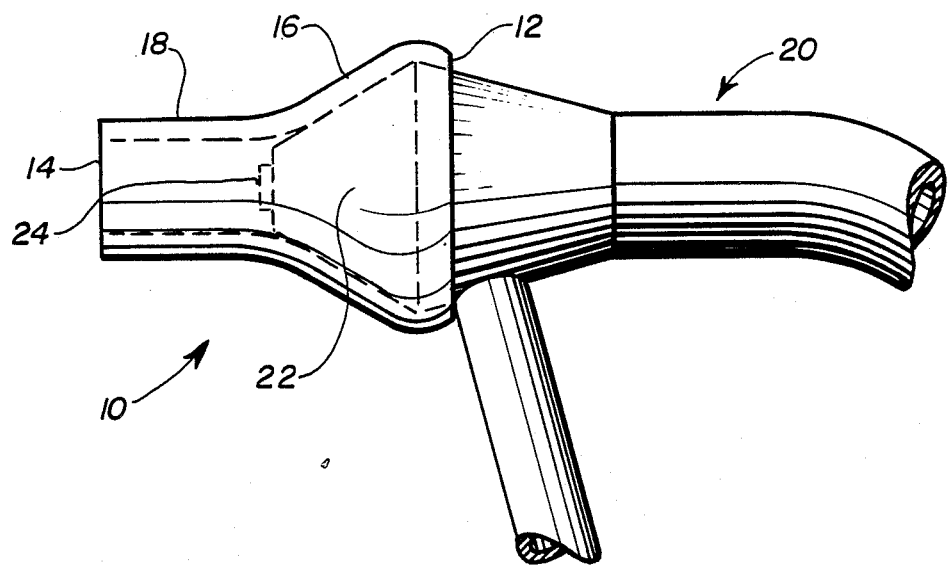
FIG. 1 is a side, cut-a-way view of the apparatus of the invention attached to a handpiece.

With reference now to FIG. 1, the apparatus of the invention comprises a spray shield 10 which is adapted to be attached to a handpiece end 20.

A number of dental handpieces which may employ the spray shield of the invention are disclosed in copending U.S. Ser. No. 40,649 having the same assignee. The disclosure of U.S. Ser. No. 40,649 is incorporated herein by reference. It is to be understood that the use of the apparatus of the invention is not limited to the particular handpieces described therein.

Spray shield 10 comprises a first end 12 which is adapted to fit onto handpiece tip 22 of handpiece end 20, second end 14 extended away from the handpiece tip 22, first portion 16 which covers the handpiece tip 22 from extreme end 24 thereof to first end 12, and second portion 18 which is the portion of spray shield 10 which is between extreme tip 24 of handpiece 20 and second end 14 of spray shield 10. In the illustrated embodiment the edges of second end 14 will be rounded so that second end 14 will not harm gingival tissue when spray shield 14 is pressed against such tissue.

Although illustrated handpiece end 20 comprises part of an air-abrasive handpiece, it is understood that the spray shield 10 of the invention may be used with any dental handpiece that delivers material to a dental working area with high speed or under pressure such that there is a tendency for a spray or mist of material to be formed in the atmosphere or for which it is desirable to direct a spray.

As used herein, "working area" means the surface which is intended to be treated while using the apparatus of the invention. The "working end" of the handpiece is the end that dispenses the material that is used to treat the working area. The "working distance" is the nominal optimum effective distance of the working end of the handpiece from the working area.

In the preferred embodiment, spray shield 10 will be made of an elastomeric material which stretched to a degree sufficient for end 12 to fit over handpiece tip 22 and provide a tight fit thereon.

It will be recognized by those skilled in the art that other means for attaching spray shield 10 to handpiece end 20 may be used, and accordingly, materials other than elastomeric materials may be used for making spray shield 10.

In the preferred embodiment, spray shield 10 will be made having first portion 16 of a length that substantially optimizes the working effectiveness of handpiece end 20 by adapting said length to the optimum working distance of the handpiece for a particular area of the mouth or for a particular patient. If the handpiece is held too far away from the working area, the dispersion of the spray makes it difficult to avoid hitting restorative areas and sensitive gingival areas with the spray. When the optimum working distance has been established, and second portion 18 is made a length corresponding to the optimum working distance, the practitioner needs only to keep second end 14 of spray shield 10 in close proximity to the working area to obtain an efficient treatment by keeping the handpiece a constant distance from the working area.

It will be recognized by those skilled in the art that a fixed length spray shield may be used on the handpiece and that a number of different sizes of spray shields may be provided and used in cases where the effective working distances of the handpiece varies.

Accordingly, the spray shield of the invention will preferably be from about 9 to 13 mm long, and more preferably will be about 10 to 12 mm long, and in the preferred embodiment will be about 11 mm long. The working length of the spray shield of the invention may vary depending on the kind of material that is dispensed from the handpiece and in the case of an air-abrasive handpiece will be about 3 to 5 mm, and preferably will be about 4 mm.

It is important for the operation of the spray shield that the wall thickness of the spray shield not be too thick or too thin. If the walls are too thin, the walls may collapse when contacted with gingival tissue or a restorative, and block off the flow of the spray. If the walls are too thick, it will be difficult to stretch the spray shield to fit on the handpiece nozzle. In the preferred embodiment the spray shield will have an O.D. of about 0.154 inch and an I.D. of about 0.094 inch. A handpiece nozzle of a type typically used with the spray shield of the invention has a diameter of about 0.250 inch.

In its operation spray shield 10 surrounds the gas and liquid and optional particle spray and contains the gas and liquid and optional particle spray during the initial dispensing thereof, until the spray has impinged on the tooth surface and the pressure of the initial dispensing has diminished. It is the initial pressure of the dispensing of the spray that causes the problem of airborne particles and mist. By containing the particles in the portion of the shield between the end of the handpiece and the working area, the amount of airborne liquid and abrasive particles are substantially reduced, and the spray itself can be more easily directed to the working area.

As used herein, "directed" is intended to describe the procedure by which the spray shield of the invention may be used to contact at an angle against and be moved along the edge of the gums or a restorative material so that the spray of material is at an angle directed away from the gums or restorative material.

In one embodiment of the spray shield, the shield may be adapted to be adjustable on the end of handpiece 20 to provide for a longer or shorter second portion 18 to provide for a longer or shorter working distance. This may be done by simply sliding spray shield 10 up and down handpiece end 22, or a number different length spray shields 10 may be provided. Different working distances may be desirable for working in different areas of the mouth.

The present invention represents an improvement over prior art handpieces whereby spray shield 10 provides for a more effective, cleaner use of said handpieces for cleaning dental surfaces. The present invention is therefore drawn to a dental handpiece having means of applying a liquid or a liquid and abrasive powder to a working area in the mouth wherein the liquid or liquid and abrasive powder is applied under pressure to said working area, wherein the improvement to the handpiece is the attachment of the spray shield of the invention to the working end of the handpiece.

In the method of using the spray shield of the invention, the spray shield is provided in the form of a tubular member. A first portion of the tubular member is adapted to be attached to a working end of a dental handpiece, and subsequently is attached to the working end of a dental handpiece such that a second portion of the tubular member will extend a distance beyond the working end of the handpiece. Preferably, the optimum working distance of the dental handpiece from the working area in the mouth will be established and the second portion of the tubular member will be adjusted to have a length such that it extends beyond the working end of the handpiece substantially the optimum working distance thereof.

The method of the invention, in its preferred embodiment, will comprise the further steps of making the spray shield from an elastomeric material, and most preferably, the elastomeric material will be transparent.

In using the spray shield, the handpiece will be held so that the spray shield is in close proximity to the working area of a tooth while the air-abrasive powder/water mixture is dispensed. While working near gingival tissue or restorative material, the rounded edge of the spray shield can be contacted against the gingival tissue or restorative material and directed at an angle from said tissue or said restorative material, thereby preventing the tissue or restorative material from being hit with the spray.

The apparatus and method of the present invention minimizes the amount of particles that escape into the atmosphere by containing or retaining the spray of materials within the apparatus until the initial power of their initial dispensing from the handpiece is diminished. The apparatus of the invention also make it possible for the practitioner to more precisely control the area of impact of the spray since the spray can be directed through the apparatus of the invention, making it easier to avoid hitting restorative areas and gingival tissue with the spray. The apparatus also increases the efficiency of the procedure since the second end of the tubular member in close proximity to the working area provides a reference point for maintaining what may be considered the optimum working distance of the handpiece from a particular working surface. Also, the practitioner may use the apparatus of the invention for better cleaning posterior regions of the mouth by adapting the length of the second portion of the spray shield to what may be considered the optimum length, and holding the second end directly against or on an angle against posterior teeth to provide a cleaning thereof.

To avoid contamination between patients and avoid the necessity of sterilizing the spray shield, it is preferred that the spray shield of the invention be disposable.

While present embodiments of the invention and methods of practicing the same have been illustrated and described, it will be recognized by those skilled in the art that this invention may be otherwise variously embodied and practiced within the scope of the following claims.

What is claimed is:

1. In a dental handpiece having means for applying a liquid or a liquid and abrasive powder to a working area of the mouth in which said liquid or liquid and abrasive powder is applied under pressure to said working area, wherein the improvement comprises a tubular member having a first end attached to the working end of said handpiece, and a second end adapted to extend a distance beyond the working end of said handpiece, wherein said tubular member is adapted to direct and restrain material dispensed from said handpiece and to maintain a substantially optimum working distance between said working end of said handpiece and a working area on which said dental handpiece is used.

2. The dental handpiece according to claim 1 in which said tubular member is elastomeric to a degree sufficient to stretch and fit over the working end of said handpiece and to be held tightly on the end of said handpiece.

3. The dental handpiece according to claim 1 in which said first end is part of a first portion which is adapted to fit on the end of said handpiece and said second end is part of a second portion which extends from the end of said handpiece to said second end, and the length of said second portion is adjustable so that the distance from the working end of the handpiece to the working area provides an optimum and constant working distance for a particular working area when said second end is held in close proximity to the working area.

4. The dental handpiece of claim 1 in which said tubular member is transparent elastomeric material.

5. A method of using a spray shield on a dental handpiece comprising the steps of
    (a) providing said spray shield in the form of a tubular member
    (b) adapting a first portion of said tubular member to be attached to a working end of said dental handpiece
    (c) attaching said tubular member to said working end of said dental handpiece such that a second portion of said tubular member extends a distance beyond said working end, and
    (d) establishing the length of said second portion to be substantially an optimal working distance of said working end of said handpiece from a working area in the mouth.

6. The method of claim 5 which comprises the further steps of
    (a) pressing said second portion of said spray shield at an angle against and directed away from gingival tissue or restorative material and
    (b) activating an air-abrasive powder/water spray to affect cleaning of a tooth surface while preventing damage to said gingival tissue or to said restorative material.

* * * * *